United States Patent
McIntyre

(10) Patent No.: US 6,696,592 B2
(45) Date of Patent: Feb. 24, 2004

(54) METHODS OF MAKING 21-[4'-(NITROOXYALKYL)BENZOATE] CORTICOSTEROID DERIVATIVES AND INTERMEDIATES USEFUL IN THE SYNTHESIS THEREOF

(75) Inventor: Donald G. McIntyre, Raleigh, NC (US)

(73) Assignee: NicOx-S.A., Sophia Antipolis (FR)

( * ) Notice: Subject to any disclaimer, the term of this patent is extended or adjusted under 35 U.S.C. 154(b) by 65 days.

(21) Appl. No.: 10/152,433

(22) Filed: May 21, 2002

(65) Prior Publication Data

US 2003/0153545 A1 Aug. 14, 2003

Related U.S. Application Data

(60) Provisional application No. 60/292,792, filed on May 22, 2001.

(51) Int. Cl.[7] .............................................. C07C 205/00
(52) U.S. Cl. ........................................................ 560/23
(58) Field of Search .......................................... 560/23

(56) References Cited

U.S. PATENT DOCUMENTS

| | | | |
|---|---|---|---|
| 4,956,482 A | 9/1990 | Hofmeister et al. | |
| 5,599,807 A | 2/1997 | Ogata et al. | |
| 5,621,000 A | 4/1997 | Arena et al. | |
| 5,780,495 A | 7/1998 | Del Soldato | |
| 5,861,426 A | 1/1999 | Del Soldato et al. | |
| 5,985,862 A | 11/1999 | Tjoeng et al. | |
| 6,040,341 A | 3/2000 | Del Soldato et al. | |

FOREIGN PATENT DOCUMENTS

| | | |
|---|---|---|
| DE | 27 03 543 | 7/1978 |
| DE | 2703543 A1 | 7/1978 |
| GB | 834 400 | 5/1960 |
| WO | WO 98/15568 A2 | 4/1998 |
| WO | WO 00/61604 A2 | 10/2000 |

OTHER PUBLICATIONS

Haiza, Mohammed A., et al., "O–Nitromandelic Acid: A Chiral Solvating Agent for the NMR Determination of Chiral Diamine Enatiomeric Purity", Chirality 9:556–562, 1997.

Paul–Clark, Mark, et al., "21–NO–prednisolone is a novel nitric oxide–releasing derivative of prednisolone with enhanced anti–inflammatory properties.", British Journal of Pharmacology, 2000, vol. 131, pp. 1345–1354, Macmillan Publishers.

*Primary Examiner*—Paul J. Killos
(74) *Attorney, Agent, or Firm*—Burns, Doane, Swecker & Mathis, L.L.P.

(57) ABSTRACT

The present invention provides methods of making 21-[4'-(nitrooxyalkyl)benzoate] corticosteroid derivatives according to the following general reaction scheme:

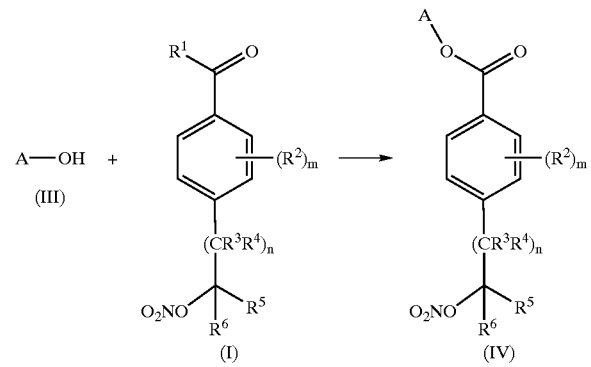

The invention also provides intermediates useful in making such 21-[4'-(nitrooxyalkyl)benzoate] corticosteroid derivatives as well as methods for making such intermediates.

59 Claims, No Drawings

METHODS OF MAKING 21-[4'-(NITROOXYALKYL)BENZOATE] CORTICOSTEROID DERIVATIVES AND INTERMEDIATES USEFUL IN THE SYNTHESIS THEREOF

CROSS-REFERENCE TO RELATED APPLICATIONS

This application claims the priority benefit of U.S. Provisional Application No. 60/292,792 filed May 22, 2001, the entire disclosure of which is incorporated herein by reference.

FIELD OF THE INTENTION

The present invention relates to methods for making 21-[4'-(nitrooxyalkyl)benzoate] corticosteroid derivatives and also relates to intermediates useful in making such compounds.

BACKGROUND OF THE INVENTION

Corticosteroids are known to have anti-inflammatory and immunomodulatory properties useful in the treatment of numerous diseases, including autoimmune and inflammatory diseases. However, treatment with corticosteroids may cause undesirable side-effects.

Steroid nitrate ester ($ONO_2$) derivatives have been used as nitric oxide donors to potentially increase the therapeutic actions of and counteract or lessen the side-effects of corticosteroids. For example, U.S. Pat. No. 5,985,862 discloses pharmaceutical compositions having steroid nitrate ester ($ONO_2$) derivatives and their use in treating undesired smooth muscle contractions and inflammatory diseases. The '862 patent also discloses using nitric acid and acetic acid to form certain steroid nitrate ester derivatives.

WO 98/15568 entitled "Nitrate Esters of Corticoid Compounds and Pharmaceutical Applications Thereof" relates to steroid-structured compounds having anti-inflammatory, immunodepressive, and angiostatic activities. One of the disclosed synthetic routes includes the use of silver nitrate ($AgNO_3$) in acetonitrile. However, silver nitrate is known to be hazardous and toxic if ingested.

It would be desirable to provide an efficient and low-cost method of making 21-[4'-(nitrooxyalkyl)benzoate] corticosteroid derivatives without using heavy metal compounds such as silver nitrate.

SUMMARY OF THE INVENTION

The present invention relates to methods for making 21-[4'-(nitrooxyalkyl)benzoate] corticosteroid derivatives and also relates to intermediates useful in the methods for making such compounds.

In one aspect, a method for making a 21-[4'-(nitrooxyalkyl)benzoate] corticosteroid derivative is provided comprising:

reacting:
(a) a 21-hydroxyalkyl corticosteroid;
(b) a compound of formula (I):

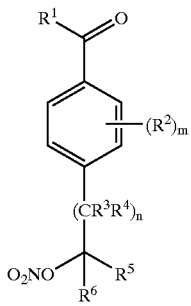

(I)

wherein:
$R^1$ is selected from the group consisting of OH, Cl, Br, F, I, and $—OC(O)R^{10}$;
m is an integer from 0 to 4;
n is an integer from 0 to 5;
$R^2$ is independently selected at each occurrence from the group consisting of amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and $—OR^7$;
$R^3$ and $R^4$ are independently selected at each occurrence from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and $—OR^7$;
$R^5$ and $R^6$ are independently selected from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and $—OR^7$;
$R^7$ is independently selected at each occurrence from the group consisting of hydrogen, $—C(O)R^8$, and $—C(O)NR^8R^9$;
$R^8$ and $R^9$ are independently selected at each occurrence from the group consisting of hydrogen and $C_{1-6}$ alkyl; and
$R^{10}$ is selected from the group consisting of $C_{1-6}$ alkyl, $C_{1-6}$ chloroalkyl, alkoxy-substituted $C_{1-6}$ alkyl, and aryl; and
(c) a coupling agent or a base; with the proviso that when $R^1$ is OH the coupling agent is used and when $R^1$ is Cl, Br, F, I, or $—OC(O)R^{10}$ the base is used.

In another aspect of the invention, a two-step method for producing a 21-[4'-(nitrooxyalkyl)benzoate] corticosteroid derivative is provided comprising:
(a) reacting a compound of formula (II):

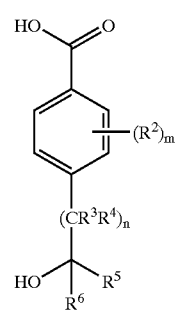

(II)

with acetic anhydride and nitric acid to form a compound of formula (IA):

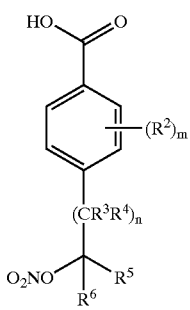

and (b) reacting the compound of formula (IA) with a 21-hydroxyalkyl corticosteroid and a coupling agent to produce a 21-[4'-(nitrooxyalkyl)benzoate] corticosteroid derivative; wherein m, n, and $R^2$–$R^6$ are as defined above.

In yet another aspect, a three-step method for producing a 21-[4'-(nitrooxyalkyl)benzoate] corticosteroid derivative is provided comprising:

(a) reacting a compound of formula (II):

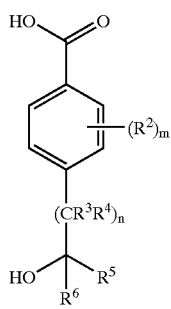

with acetic anhydride and nitric acid to form a compound of formula (IA):

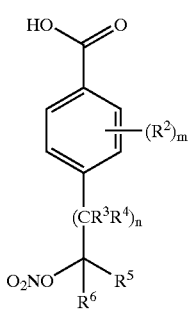

(b) reacting the compound of formula (IA) with a halogenating agent to form a compound of formula (IB):

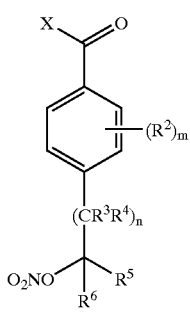

wherein X is selected from the group consisting of Cl, Br, F, and I; and (c) reacting the compound of formula (IB) with a 21-hydroxyalkyl corticosteroid and a base to produce a 21-[4'-(nitrooxyalkyl)benzoate] corticosteroid derivative; wherein m, n, and $R^2$–$R^6$ are as defined above.

In a further aspect, another three-step method for producing a 21-[4'-(nitrooxyalkyl)benzoate] corticosteroid derivative is provided comprising:

(a) reacting a compound of formula (II):

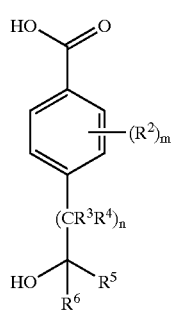

with acetic anhydride and nitric acid to form a compound of formula (IA):

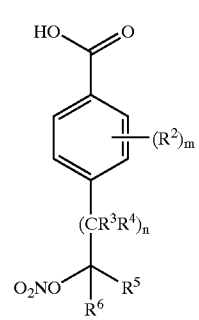

(b) reacting the compound of formula (IA) with an acid anhydride or an acid chloride to form a compound of formula (IC):

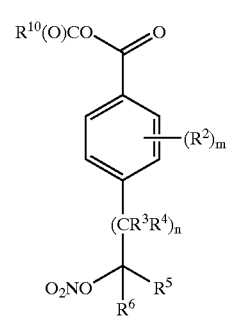

and (c) reacting the compound of formula (IC) with a 21-hydroxyalkyl corticosteroid and a base to produce a 21-[4'-(nitrooxyalkyl)benzoate] corticosteroid derivative; wherein m, n, and $R^2$–$R^6$, and $R^{10}$ are as defined above.

In yet a further aspect, the present invention provides intermediates of formula (I) useful in the methods for making 21-[4'-(nitrooxyalkyl)benzoate] corticosteroid derivatives as well as processes for making such intermediates.

DETAILED DESCRIPTION OF THE INVENTION

The present invention relates to methods for making 21-[4'-(nitrooxyalkyl)benzoate] corticosteroid derivatives and also relates to intermediates useful in the methods for making such compounds. Prior to describing this invention in further detail, however, the following terms will first be defined.

Definitions:

Unless otherwise stated, the following terms used in the specification and claims have the meanings given below:

"Alkyl" means a branched or straight hydrocarbon group having the general formula $C_nH_{2n+1}$, where n is an integer equal to or greater than 1.

"$C_{1-6}$ alkyl" means an alkyl group having from 1 to 6 carbon atoms, such as methyl, ethyl, t-butyl, and the like.

"Amino" refers to the group —$NH_2$.

"Hydroxy" refers to the group —OH.

"Thioalkyl" refers to the group —S—($C_{1-6}$ alkyl).

"Alkoxy" refers to the group —O—($C_{1-6}$ alkyl), which includes, by way of example, methoxy, ethoxy, n-propoxy, iso-propoxy, n-butoxy, tert-butoxy, sec-butoxy, n-pentoxy, and the like.

"Substituted amino" means an amino group in which one or both of the hydrogens are independently replaced with a $C_{1-6}$ alkyl group, hydroxy, an alkoxy group, or a thioalkyl group.

"Halogen" means chlorine (Cl), bromine (Br), iodine (I), or fluorine (F).

"$C_{1-6}$ haloalkyl" means a $C_{1-6}$ alkyl group in which one or more of the hydrogens are independently replaced with a halogen.

"Aryl" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinione).

"$C_{1-6}$ alkylamino" means a $C_{1-6}$ alkyl group in which one or more of the hydrogens are independently replaced with an amino group.

"$C_{1-6}$ substituted alkylamino" means a $C_{1-6}$ alkyl group in which one or more of the hydrogens are independently replaced with a substituted amino group.

"21-hydroxy corticosteroid" means any synthetic or naturally-occurring corticosteroid having a hydroxy group attached to the carbon in position 21. Corticosteroids include glucocorticoids and mineralocorticoids. Examples of 21-hydroxy corticosteroids include, but are not limited to, alclometasone, aldosterone, beclomethasone, betamethasone, clocortolone, hydrocortisone, budesonide, cortisone, desoximetasone, desonide, dexamethosone, flucloronide, fludrocortisone, flumethasone, flunisolide, fluocinolone acetonide, fluocortolone, fluprednisolone, flurandrenolide, halometasone, methylprednisolone, paramethasone, prednival, prednylidene, prednisolone, prednisone, triamcinolone, and triamcinolone acetonide.

"21-hydroxy glucocorticoid" means any synthetic or naturally-occurring glucocorticoid having a hydroxy group attached to the carbon in position 21. Examples of 21-hydroxy glucocorticoids include, but are not limited to, beclomethasone, methylprednisolone, and paramethasone.

"21-[4'-(nitrooxyalkyl)benzoate] corticosteroid derivative" means a corticosteroid derivative having a 4-(nitrooxyalkyl)benzoate attached to the carbon in the 21 position of the corticosteroid via an ester linkage with the benzoate as shown and described in formula (IV) below. An example of a 21-[4'-(nitrooxyalkyl)benzoate)] corticosteroid derivative is prednisolone 21-[4'-(nitrooxymethyl) benzoate].

"Alkoxide" means a saltlike compound ROM, wherein R is a $C_{1-6}$ alkyl group and M is a Group I metal such as, for example, sodium or potassium. Alkoxides may be formed by reaction of an alcohol with a Group I metal such as sodium or potassium. Examples of alkoxides include, but are not limited to, sodium methoxide, sodium ethoxide, potassium methoxide, potassium ethoxide, potassium t-butoxide, sodium t-butoxide.

"Carbonate" means a salt of carbonic acid containing the carbonate ion, $CO_3^{2-}$. Examples of carbonates include, but are not limited to, sodium carbonate, potassium carbonate, lithium carbonate, and cesium carbonate.

"$C_{1-6}$ chloroalkyl" means a $C_{1-6}$ alkyl group in which one or more of the hydrogens are replaced with chlorine.

"Alkoxy-substituted $C_{1-6}$ alkyl" means a $C_{1-6}$ alkyl group in which one or more of the hydrogens are independently replaced with an alkoxy group.

"Acid anhydride" means a compound of the formula (Q—C(O))$_2$O, wherein Q is selected from the group consisting of a $C_{1-6}$ alkyl group, a $C_{1-6}$ chloroalkyl group, an alkoxy-substituted $C_{1-6}$ alkyl group, and an aryl group. Examples of acid anhydrides include, but are not limited to, acetic anhydride, chloroacetic anhydride, and dichloroacetic anhydride.

"Acid chloride" means a compound of the formula Z—C(O)Cl, wherein Z is selected from the group consisting of a $C_{1-6}$ alkyl group, a $C_{1-6}$ chloroalkyl group, an alkoxy-substituted $C_{1-6}$ alkyl group, and an aryl group. Examples of acid chlorides include, but are not limited to, acetyl chloride, pivaloyl chloride, chloroacetyl chloride, dichloroacetyl chloride, trichloroacetyl chloride, methoxyacetyl chloride, and benzoyl chloride.

General Reaction Scheme

The general reaction scheme of the invention for producing a 21-[4'-(nitrooxyalkyl)benzoate] corticosteroid derivative is represented as follows:

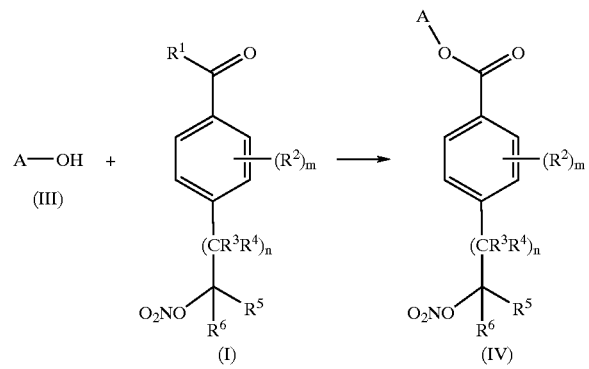

wherein:
A—OH is a 21-hydroxy corticosteroid;
$R^1$ is selected from the group consisting of OH, Cl, Br, F, I, and —OC(O)$R^{10}$;
m is an integer from 0 to 4;
n is an integer from 0 to 5;
$R^2$ is independently selected at each occurrence from the group consisting of amino, substituted amino, halogen, $C_{1-6}$ alkyl, $C_{1-6}$ haloalkyl, alkoxy, aryl, $C_{1-6}$ alkylamino; $C_{1-6}$ substituted alkylamino, and —O$R^7$;
$R^3$ and $R^4$ are independently selected at each occurrence from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —O$R^7$;

$R^5$ and $R^6$ are independently selected from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^7$;

$R^7$ is independently selected at each occurrence from the group consisting of hydrogen, —$C(O)R^8$, and —$C(O)NR^8R^9$;

$R^8$ and $R^9$ are independently selected at each occurrence from the group consisting of hydrogen and $C_{1-6}$ alkyl; and $R^{10}$ is selected from the group consisting of $C_{1-6}$ alkyl, $C_{1-6}$ chloroalkyl, alkoxy-substituted $C_{1-6}$ alkyl, and aryl.

The compound of formula (III) (i.e., A—OH) is preferably a 21-hydroxy glucocorticoid, and is more preferably prednisolone, which is represented by the following formula (IIIA):

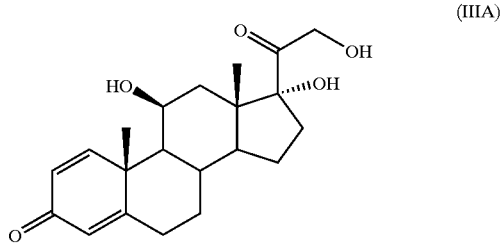

(IIIA)

$R^1$ is preferably OH, Cl, or Br, and is more preferably OH. In one preferred embodiment, in the compound of formula (I), $R^1$ is OH, m and n are 0, and $R^5$ and $R^6$ are hydrogen such that the compound of formula (I) is 4-(nitrooxymethyl)benzoic acid.

As shown in the general reaction scheme above, a 21-[4'-(nitrooxyalkyl)benzoate] corticosteroid derivative is produced by reacting (a) a compound of formula (III) (i.e., a 21-hydroxy corticosteroid A—OH), (b) a compound of formula (f), and (c) either a coupling agent or a base, depending upon the substituent $R^1$. By way of example, when $R^1$ is OH, (a) a compound of formula (I), (b) a corticosteroid of formula (III), and (c) a suitable coupling agent are reacted. Suitable coupling agents include, but are not limited to, 1,3-diisopropylcarbodiimide, 1,3-dicyclohexylcarbodiimide, 1-(3-dimethylaminopropyl)-3-ethylcarbodiimide hydrochloride, 2-chloro-1-methylpyridiniurn iodide, and N, N-dimethylformamide neopentylacetal. The preferred coupling agent is 1-(3-dimethylaminopropyl)-3-ethylcarbodiimide hydrochloride.

By way of further example, when $R^1$ is Br, Cl, F, I, or —$OC(O)R^{10}$ (a) a compound of formula (I), (b) a corticosteroid of formula (III), and (c) a suitable base are reacted. Suitable bases include, but are not limited to, triethylamine, pyridine, diisopropyl ethylamine, tetramethylguanidine, 1,5-diazabicyclo[4.3.0]non-5-ene, 1,8-diazabicyclo[5.4.0]undec-7-ene, alkoxides, and carbonates. The preferred base is triethylamine.

The reaction is preferably carried out in the presence of a catalyst. That is, the compound of formula (I) is preferably reacted with a 21-hydroxy corticosteroid, either a coupling agent or a base, and a suitable catalyst. Suitable catalysts include, but are not limited to, 4-dimethylaminopyridine and N, N-dimethylaniline. The preferred catalyst is 4-dimethylaminopyridine.

The reaction is also preferably carried out in an anhydrous solvent or solvent mixture such as, for example, pyridine, tetrahydrofuran, dimethylformamide, sulfolane, acetone, acetonitrile, ethyl acetate, dioxane, methyl ethyl ketone, ether, methyl t-butyl ether, chloroform, dichloromethane, or mixtures thereof The preferred solvent is acetone.

The reaction is typically carried out in a temperature range from about 0° C. to about 50° C., and is preferably carried out at about 25° C. The reaction is typically carried out for about 15 minutes to about 24 hours, and is preferably carried out from about 5 hours to about 8 hours.

Materials

The 21-hydroxy corticosteroids of formula (III) used in the present invention are generally commercially available or may be obtained according to processes known in the art.

A compound of formula (I) above may be synthesized in one or two steps, depending upon the desired $R^1$ group of the compound (wherein $R^1$ is selected from the group consisting of OH, Cl, Br, F, I, and —$OC(O)R^{10}$). The following synthetic scheme illustrates the one or two steps needed to produce a compound of formula (I) wherein $R^1$ is OH, Cl, Br, F, or I:

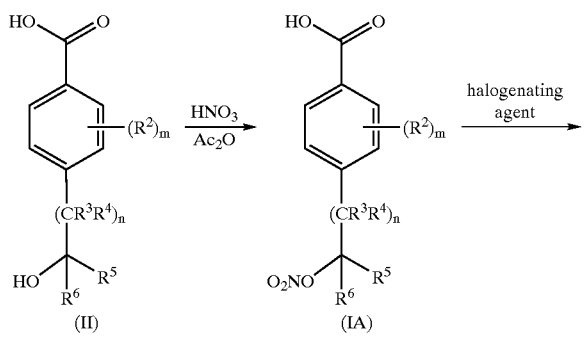

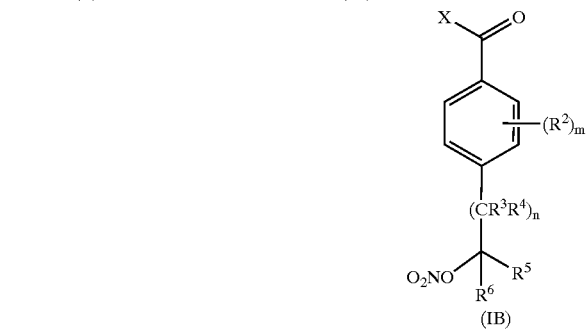

wherein:
X is selected from the group consisting of Cl, Br, I, or F; and $R^2$, $R^3$, $R^4$, $R^5$, $R^6$, m, and n are as defined above in the general reaction scheme.

In the first step, the compound of formula (II) is reacted with nitric acid ($HNO_3$) and acetic anhydride ($Ac_2O$) to form the nitroester acid compound of formula (IA). This first step generates a compound of formula (I) in the general reaction scheme above wherein $R^1$ is OH. This reaction is typically carried out in a temperature range from about −50° C. to about 0° C., and is preferably carried out from about −30° C. to about −10° C. The reaction is typically carried out for about 1 minute to about 24 hours, and is preferably carried out for about 1 hour to about 3 hours.

In order to form a compound of formula (I) in the general reaction scheme above wherein $R^1$ is Cl, Br, I, or F (i.e., $R^1$ is X), the second step must be carried out. When $R^1$ is Cl, Br, I, or F in the compound of formula (I) (i.e., when X is Cl, Br, I, or F in the compound of formula (IB)), the compound of formula (IA) is halogenated with a suitable halogenating agent to form the acid halide of formula (IB). Suitable halogenating agents include, but are not limited to, the following: chlorinating agents—thionyl chloride, N-chlorosuccinimide, oxalyl chloride, chlorine, potassium pentachloride, and potassium trichloride; brominating agents—N-bromosuccinimide, bromine, potassium tribromide, potassium pentabromide, and oxalyl bromide; fluorinating agents—potassium fluoride, polyhydrogen fluoride-pyridine, diethylaminosulfurtrifluoride, hydrogen fluoride, and cyanuric fluoride; iodinating agents—N-iodosuccinimide and iodine. The reaction is typically carried in a temperature range from about −10° C. to about 30° C., and is preferably carried out in a temperature range from about 0° C. to about 5° C. The reaction is typically carried out for about 1 minute to about 24 hours, and is preferably carried out for about 30 minutes.

In order to form a compound of formula (I) in the general reaction scheme above wherein $R^1$ is —OC(O)$R^{10}$, an alternate second step must be carried out. The following synthetic scheme illustrates the first step described above and the alternate second step:

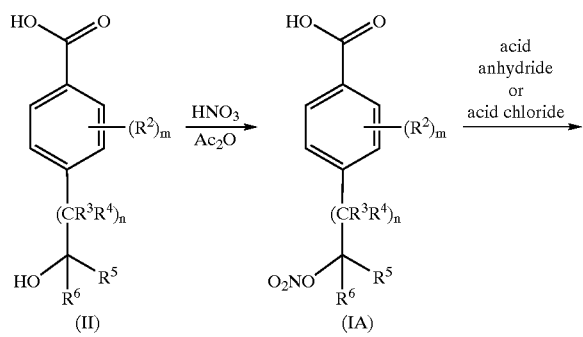

wherein:
$R^2$, $R^3$, $R^4$, $R^5$, $R^6$, $R^{10}$, m, and n are as defined above in the general reaction scheme.

After performing the first step as described above, the compound of formula (IA) is reacted with a suitable acid anhydride or a suitable acid halide to form the compound of formula (IC). Suitable acid anhydrides include, but are not limited to, acetic anhydride, chloroacetic anhydride, and dichloroacetic anhydride. Suitable acid chlorides include, but are not limited to, acetyl chloride, pivaloyl chloride, chloroacetyl chloride, dichloroacetyl chloride, trichloroacetyl chloride, methoxyacetyl chloride, and benzoyl chloride. The reaction is typically carried out in a temperature range from about −10° C. to about 30° C., and is preferably carried out in a temperature range from about 0° C. to about 5° C. The reaction is typically carried out for about 1 minute to about 24 hours, and is preferably carried out for about 30 minutes.

Illustrative Embodiments

In one aspect of the invention and as discussed above in the general reaction scheme, a one-step method is used to produce a 21-[4'-(nitrooxyalkyl)benzoate] corticosteroid derivative. As discussed above, the method comprises reacting (a) a compound of formula (III), (b) a compound of formula (I), and (c) either a coupling agent (when $R^1$ is OH in the compound of formula (I)) or a base (when $R^1$ is Cl, Br, F, I, or —OC(O)$R^{10}$ in the compound of formula (I)). In a preferred embodiment, the compound of formula (III) is prednisolone and, in formulas (I) and (IV), $R^1$ is OH, m and n are 0, and $R^5$ and $R^6$ are hydrogen such that the compounds of formulas (I) and (IV) are respectively 4-(nitrooxymethyl)benzoic acid and prednisolone 21-[(4'-(nitrooxymethyl)benzoate]. Prednisolone 21-[(4'-(nitrooxymethyl)benzoate] is shown below as formula (IVA):

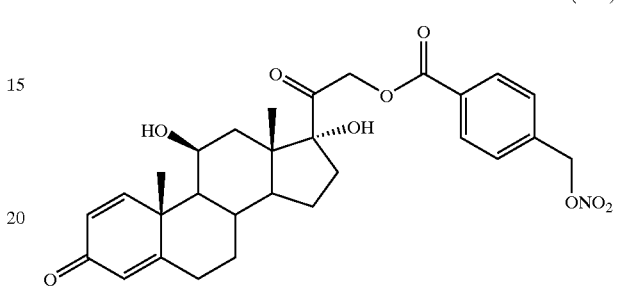

In another aspect, a two-step method is used wherein a compound of formula (II) is reacted with nitric acid and acetic anhydride to form a nitroester acid of compound (IA). The compound of formula (IA) is reacted with a 21-hydroxy corticosteroid (the compound of formula (III)) and a coupling agent to form a 21-[4'-(nitrooxyalkyl)benzoate] corticosteroid derivative of formula (IV). The synthetic scheme is shown as follows:

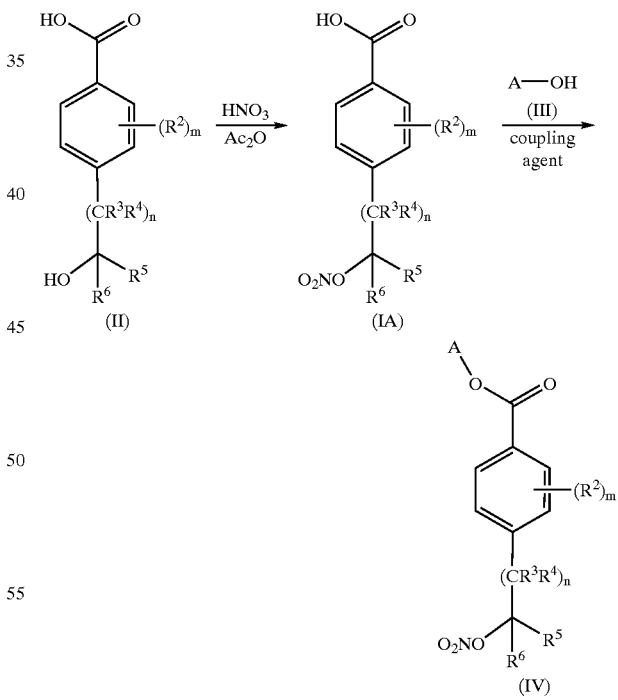

In a preferred embodiment, the 21-hydroxy corticosteroid of formula (I) is prednisolone and, in formulas (II), (IA), and (IV), m and n are 0 and $R^5$ and $R^6$ are hydrogen such that the compounds of formulas (II), (IA), and (IV) are respectively 4-(hydroxymethyl)benzoic acid, 4-(nitrooxymethyl) benzoic acid, and prednisolone 21-[(4'-(nitrooxymethyl) benzoate].

In yet another aspect, a three-step method is used to generate a 21-[4'-(nitrooxyalkyl)benzoate] corticosteroid derivative. A compound of formula (II) is reacted with nitric acid and acetic anhydride to form a nitroester acid of compound (IA). The compound of formula (IA) is then halogenated with a suitable halogenating agent to form an acid halide of formula (IB). The acid halide of formula (IB) is then reacted with a 21-hydroxy corticosteroid (the compound of formula (III)) and a base to form a 21-[4'-(nitrooxyalkyl)benzoate] corticosteroid derivative of formula (IV). The synthetic scheme is shown as follows:

acid and acetic anhydride to form a nitroester acid of compound (IA). The compound of formula (IA) is then reacted with a suitable acid anhydride or a suitable acid chloride to form a compound of formula (IC). The compound of formula (IC) is then reacted with a 21-hydroxy corticosteroid (the compound of formula (III)) and a base to form a 21-[4'-(nitrooxyalkyl)benzoate] corticosteroid derivative of formula (IV). The synthetic scheme is shown as follows:

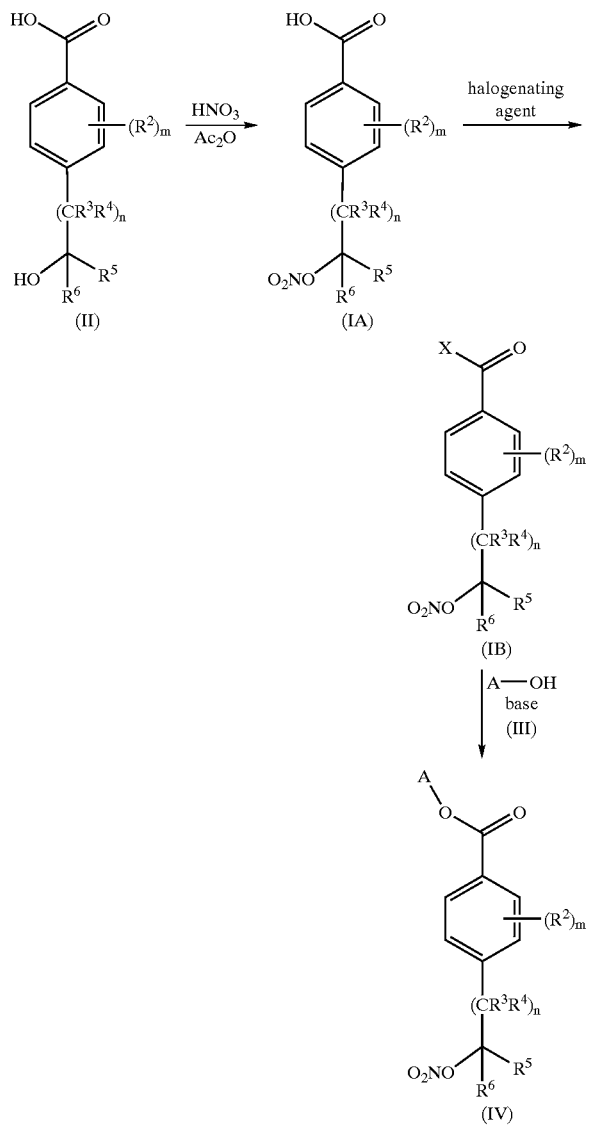

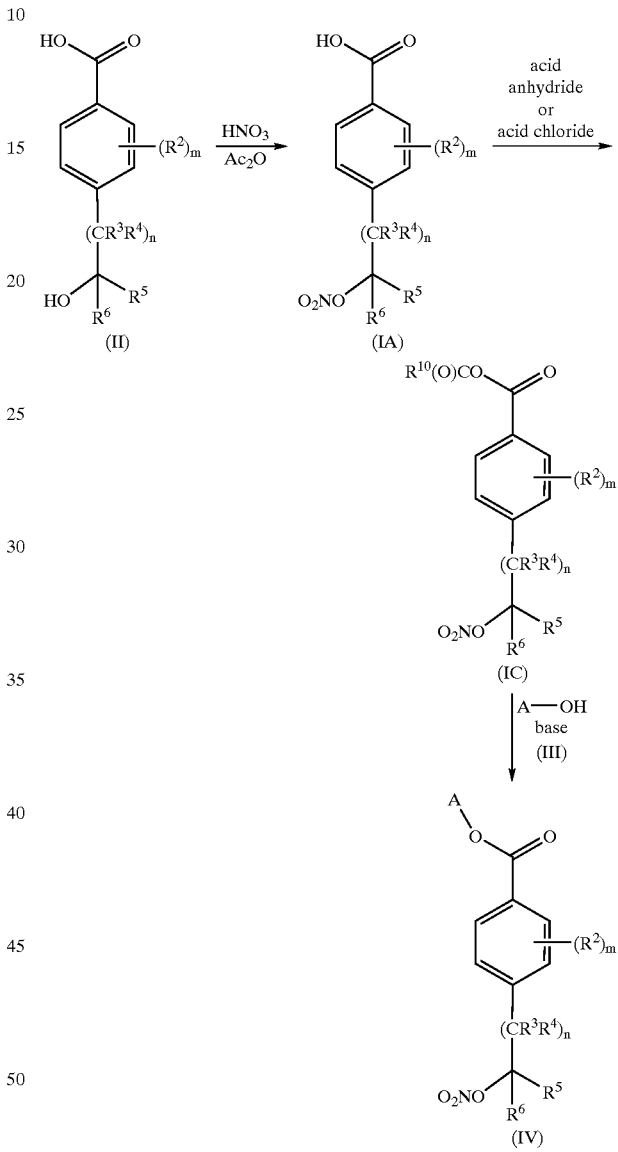

In a preferred embodiment, the 21-hydroxy corticosteroid of formula (III) is prednisolone and, in formulas (II), (IA), (IB), and (IV), m and n are 0, $R^5$ and $R^6$ are hydrogen, and, in formula (IB), X is Cl or Br such that the compounds of formulas (II), (LA), (IB), and (IV) are respectively 4-(hydroxymethyl)benzoic acid, 4-(nitrooxymethyl)benzoic acid, 4-(nitrooxymethyl)benzoyl chloride or 4-(nitrooxymethyl)benzoyl bromide, and prednisolone 21-[(4'-(nitrooxymethyl)benzoate].

In a further aspect, another three-step method is used to generate a 21-[4'-(nitrooxyalkyl)benzoate] corticosteroid derivative. A compound of formula (II) is reacted with nitric In a preferred embodiment, the 21 hydroxy corticosteroid of formula (III) is prednisolone and, in formulas (ID), (IA), (IC), and (IV), m and n are 0 and $R^5$ and $R^6$ are hydrogen such that the compounds of formulas (II), (IA), and (m) are respectively 4-(hydroxymethyl)benzoic acid, 4-(nitrooxymethyl)benzoic acid, and prednisolone 21-[(4'-(nitrooxymethyl)benzoate].

Suitable and/or preferred coupling agents, bases, halogenating agents, acid anhydrides, and acid chlorides as well as other suitable and/or preferred 21-hydroxy corticosteroids and compound substituents for each of these aspects of the invention are described above in the general reaction scheme and in the description of the materials.

EXAMPLES

The invention will be further explained by the following illustrative example that is intended to be non-limiting.

Example I

Two-Step Process for Synthesis of Prednisolone 21-[4'-(nitrooxymethyl) benzoate]

Step 1: Synthesis of 4-(nitrooxymethyl)benzoic Acid

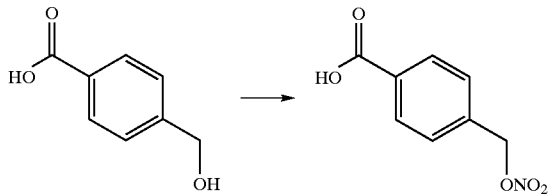

Nitric acid (760 ml) was cooled to −30° C. and acetic anhydride (1520 ml) was added portionwise with stirring. This mixture was stirred at −30° C. for 15 minutes. 4-(Hydroxymethyl)benzoic acid (400 g, 2.63 moles) slurried in acetic anhydride (1520 ml) was added and the beaker was rinsed with the remaining acetic anhydride (800 ml). After 2 hours at ~−10° C., the reaction was complete as evidenced by high performance liquid chromatography (HPLC) analysis. The reaction mixture was poured into water (10 L) and stirred for 30 minutes. The resulting white solid was filtered and washed with water (3×1.5 L) and dried overnight. The reaction was repeated and the combined resulting white solid (859 g, 83% yield), which was approximately 100% pure by HPLC analysis, was used without further purification in Step 2 described below.

The white solid (4-(nitrooxymethyl)benzoic acid) was characterized using proton nuclear magnetic resonance ($^1$H NMR). The following chemical shifts were reported (referenced from dimethyl sulfoxide (DMSO)), as follows in parts per million (ppm): $^1$H NMR (DMSO) 5.665 (2H, s), 7.581 (2H, d), 7.984 (2H, d).

Step 2: Synthesis of Prednisolone 21-[4'-(nitrooxymethyl) benzoate]

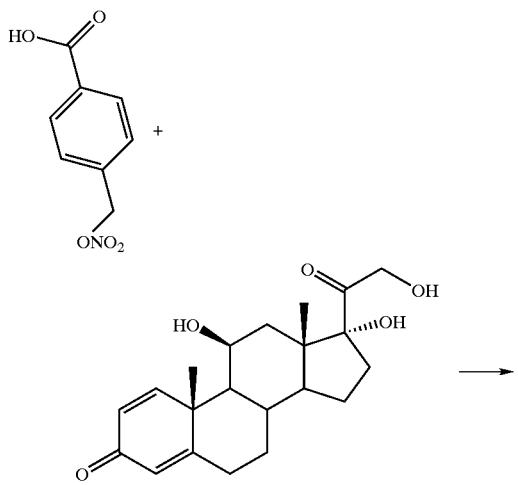

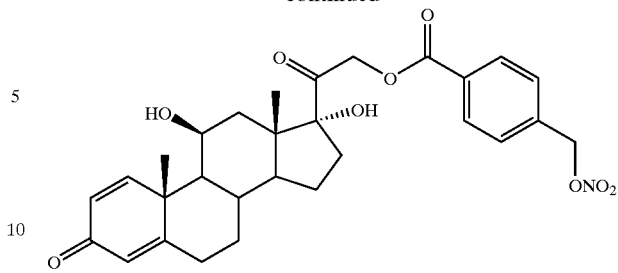

Prednisolone (1104 g, 3.06 moles), 4-(nitrooxymethyl) benzoic acid (785.5 g, 3.98 moles), and catalytic 4-(dimethylamino)pyridine (10 g) were combined in acetone (11 L). 1-(3-dimethylaminopropyl)-3-ethylcarbodiimide hydrochloride (618 g, 3.98 moles) was added in one portion. After 5 hours, the reaction was worked up. The solvent was removed from the reaction mixture, water (4 L) was added, and the mixture was stirred for 15 minutes, after which time the water was removed. Ethyl acetate: tetrahydrofuran (8:2) (3L) was added and the mixture was stirred for 30 minutes. This washing was repeated with 4 L of solvent (i.e., ethyl acetate: tetrahydrofuran (8:2)). The mixture was filtered and the resulting white solid was dried. The white solid (803 g, 48% yield) was 94.6% pure by HPLC analysis and had a melting point of 221–223° C. The white solid was characterized using proton nuclear magnetic resonance ($^1$H NMR). The following chemical shifts were reported, (referenced from dimethyl sulfoxide (DMSO)), as follows in parts per million (ppm): $^1$H NMR (DMSO) 0.838 (3H, s), 1.402 (3H, s), 5.19 (2H, dd), 5.687 (2H, s), 5.924 (1H, s), 6.174 (1H, d), 7.339 (1H, d), 7.639(2H, d), 8.042 (2H, d).

While the invention has been described in detail and with reference to specific embodiments thereof, it will be apparent to one skilled in the art that various changes and modifications can be made without departing from the spirit and scope of the invention.

What is claimed is:

1. A method for making a 21-[4'-(nitrooxyalkyl)benzoate] corticosteroid derivative comprising:

reacting:
(a) a 21-hydroxyalkyl corticosteroid;
(b) a compound of formula (I):

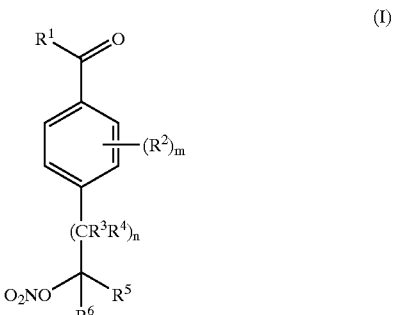

(I)

wherein:
R$^1$ is selected from the group consisting of OH, Cl, Br, F, I, and —OC(O)R$^{10}$;
m is an integer from 0 to 4;
n is an integer from 0 to 5;
R$^2$ is independently selected at each occurrence from the group consisting of amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^7$;

$R^3$ and $R^4$ are independently selected at each occurrence from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^7$;

$R^5$ and $R^6$ are independently selected from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^7$;

$R^7$ is independently selected at each occurrence from the group consisting of hydrogen, —$C(O)R^8$, and —$C(O)NR^8R^9$;

$R^8$ and $R^9$ are independently selected at each occurrence from the group consisting of hydrogen and $C_{1-6}$ alkyl; and $R^{10}$ is selected from the group consisting of $C_{1-6}$ alkyl, $C_{1-6}$ chloroalkyl, alkoxy-substituted $C_1$ alkyl, and aryl; and (c) a coupling agent or a base; with the proviso that when $R^1$ is OH the coupling agent is used and when $R^1$ is Cl, Br, F, I, or —$OC(O)R^{10}$ the base is used.

2. The method of claim 1, wherein $R^1$ is OH and the coupling agent is selected from the group consisting of 1,3-diisopropylcarbodiimide, 1,3-dicyclohexylcarbodiimide, 1-(3-dimethylaminopropyl)-3-ethylcarbodiimide hydrochloride, 2-chloro-1-methylpyridinium iodide, and N, N-dimethylformamide neopentylacetal.

3. The method of claim 1, wherein $R^1$ is Cl, Br, F, 1, or —$OC(O)R^{10}$ and the base is selected from the group consisting of triethylamine, pyridine, diisopropyl ethylamine, tetramethylguanidine, 1,5-diazabicyclo[4.3.0]non-5-ene, 1,8-diazabicyclo[5.4.0]undec-7-ene, alkoxides, and carbonates.

4. The method of claim 1, further comprising reacting (a), (b), and (c) with (d) a catalyst.

5. The method of claim 4, wherein the catalyst comprises 4-dimethylaminopyridine.

6. The method of claim 1, wherein the 21-hydroxy corticosteroid is selected from the group consisting of alclometasone, aldosterone, beclomethasone, betamethasone, clocortolone, hydrocortisone, budesonide, cortisone, desoximetasone, desonide, dexamethosone, flucloronide, fludrocortisone, flumethasone, flunisolide, fluocinolone acetonide, fluocortolone, fluprednisolone, flurandrenolide, halometasone, methylprednisolone, paramethasone, prednival, prednylidene, prednisolone, prednisone, triamcinolone, and triamcinolone acetonide.

7. The method of claim 1, wherein the 21-hydroxy corticosteroid comprises a 21-hydroxy glucocorticoid.

8. The method of claim 7, wherein the 21-hydroxy glucocorticoid comprises prednisolone.

9. The method of claim 1, wherein m is 0, n is 0, $R^5$ is hydrogen, and $R^6$ is hydrogen.

10. The method of claim 1, further comprising reacting (a), (b), and (c) with (d) a catalyst, and wherein $R^1$ is OH and the coupling agent is selected from the group consisting of 1,3-diisopropylcarbodiimide, 1,3-dicyclohexylcarbodiimide, 1-(3-dimethylaminopropyl)-3-ethylcarbodiimide hydrochloride, 2-chloro-1-methylpyridinium iodide, and N, N-dimethylformamide neopentylacetal.

11. The method of claim 10, wherein the 21-hydroxy corticosteroid comprises a 21-hydroxy glucocorticoid.

12. The method of claim 11, wherein the 21-hydroxy glucocorticoid comprises prednisolone.

13. The method of claim 12, wherein m is 0, n is 0, $R^5$ is hydrogen, and $R^6$ is hydrogen.

14. The method of claim 13, wherein the catalyst comprises 4-dimethylaminopyridine and the coupling agent comprises 1-(3-dimethylaminopropyl)-3-ethylcarbodiimide hydrochloride.

15. The method of claim 1, further comprising reacting (a), (b), and (c) with (d) a catalyst, and wherein $R^1$ is Cl or Br.

16. The method of claim 15, wherein the 21-hydroxy corticosteroid comprises a 21-hydroxy glucocorticoid.

17. The method of claim 16, wherein the 21-hydroxy glucocorticoid comprises prednisolone.

18. The method of claim 17, wherein m is 0, n is 0, $R^5$ is hydrogen, and $R^6$ is hydrogen.

19. The method of claim 18, wherein the catalyst comprises 4-dimethylaminopyridine and the base comprises triethylamine.

20. A method for producing a 21-[4'-(nitrooxyalkyl) benzoate] corticosteroid derivative comprising:

(a) reacting a compound of formula (II):

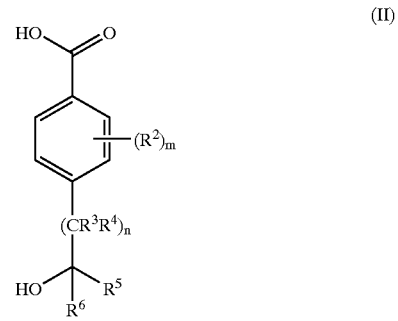

wherein:
m is an integer from 0 to 4;
n is an integer from 0 to 5;
$R^2$ is independently selected at each occurrence from the group consisting of amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^7$;

$R^3$ and $R^4$ are independently selected at each occurrence from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^1$;

$R^5$ and $R^6$ are independently selected from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^7$;

$R^7$ is independently selected at each occurrence from the group consisting of hydrogen, —$C(O)R^8$, and —$C(O)NR^8R^9$; and $R^8$ and $R^9$ are independently selected at each occurrence from the group consisting of hydrogen and $C_{1-6}$ alkyl;

with acetic anhydride and nitric acid to form a compound of formula (IA):

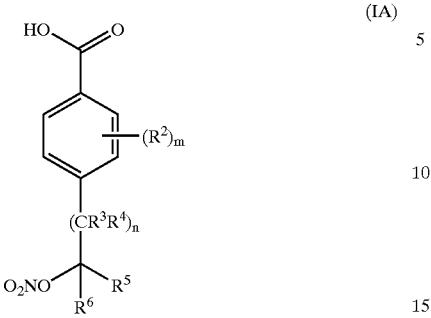

wherein m, n, $R^2$, $R^3$, $R^4$, $R^5$, and $R^6$ are as above in the compound of formula (II); and (b) reacting the compound of formula (IA) with a 21-hydroxyalkyl corticosteroid and a coupling agent to produce a 21-[4'-(nitrooxyalkyl)benzoate] corticosteroid derivative.

21. The method of claim 20, wherein the coupling agent is selected from the group consisting of 1,3-diisopropylcarbodiimide, 1,3-dicyclohexylcarbodiimide, 1-(3-dimethylaminopropyl)-3-ethylcarbodiimide hydrochloride, 2-chloro-1-methylpyridinium iodide, and N,N-dimethylformamide neopentylacetal.

22. The method of claim 20, wherein the corticosteroid, the compound of formula (IA), and the coupling agent are reacted with a catalyst.

23. The method of claim 22, wherein the catalyst comprises 4-dimethylaminopyridine.

24. The method of claim 20, wherein the corticosteroid is selected from the group consisting of alclometasone, aldosterone, beclomethasone, betamethasone, clocortolone, hydrocortisone, budesonide, cortisone, desoximetasone, desonide, dexamethosone, flucloronide, fludrocortisone, flumethasone, flunisolide, fluocinolone acetonide, fluocortolone, fluprednisolone, flurandrenolide, halometasone, methylprednisolone, paramethasone, prednival, prednylidene, prednisolone, prednisone, triamcinolone, and triamcinolone acetonide.

25. The method of claim 20, wherein the 21-hydroxy corticosteroid comprises a 21-hydroxy glucocorticoid.

26. The method of claim 25, wherein the 21-hydroxy glucocorticoid comprises prednisolone.

27. The method of claim 20, wherein m is 0, n is 0, $R^5$ is hydrogen, and $R^6$ is hydrogen.

28. The method of claim 20, wherein:
the coupling agent is selected from the group consisting of 1,3-diisopropylcarbodiimide, 1,3-dicyclohexylcarbodiimide, 1-(3-dimethylaminopropyl)-3-ethylcarbodiimide hydrochloride, 2-chloro-1-methylpyridinium iodide, and N,N-dimethylformamide neopentylacetal; and
the corticosteroid, the compound of formula (IA), and the coupling agent are reacted with a catalyst.

29. The method of claim 28, wherein the 21-hydroxy corticosteroid comprises a 21-hydroxy glucocorticoid.

30. The method of claim 29, wherein the 21-hydroxy glucocorticoid comprises prednisolone.

31. The method of claim 30, wherein m is 0, n is 0, $R^5$ is hydrogen, and $R^6$ is hydrogen.

32. The method of claim 31, wherein the catalyst comprises 4-dimethylaminopyridine and the coupling agent comprises 1-(3-dimethylaminopropyl)-3-ethylcarbodiimide hydrochloride.

33. A method for producing a 21-[4'-(nitrooxyalkyl) benzoate] corticosteroid derivative comprising:

(a) reacting a compound of formula (II):

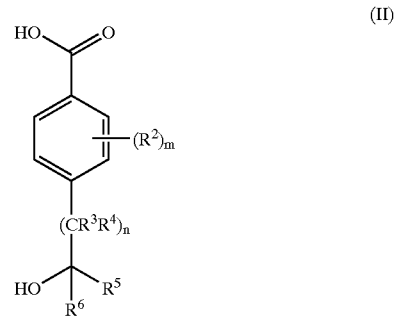

wherein:
m is an integer from 0 to 4;
n is an integer from 0 to 5;
$R^2$ is independently selected at each occurrence from the group consisting of amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^7$;

$R^3$ and $R^4$ are independently selected at each occurrence from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^7$;

$R^5$ and $R^6$ are independently selected from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^7$;

$R^7$ is independently selected at each occurrence from the group consisting of hydrogen, —$C(O)R^8$, and —$C(O)NO^8R^9$; and $R^8$ and $R^9$ are independently selected at each occurrence from the group consisting of hydrogen and $C_{1-6}$ alkyl;

with acetic anhydride and nitric acid to form a compound of formula (IA):

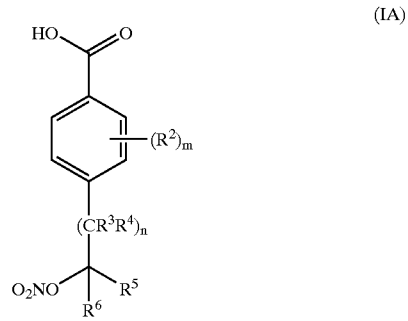

wherein m, n, $R^2$, $R^3$, $R^4$, $R^5$, and $R^6$ are as above in the compound of formula (II);

(b) reacting the compound of formula (IA) with a halogenating agent to form a compound of formula (IB):

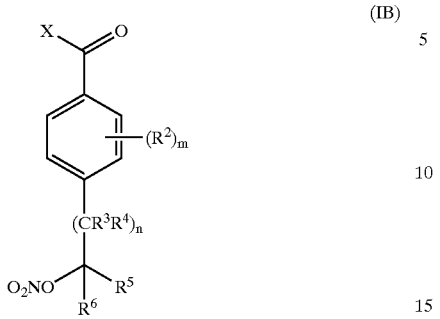

(IB)

wherein:

X is selected from the group consisting of Cl, Br, F, and I; and m, n, $R^2$, $R^3$, $R^4$, $R^5$, and $R^6$ are as above in the compound of formula (II); and (c) reacting the compound of formula (IB) with a 21-hydroxyalkyl corticosteroid and a base to produce a 21-[4'-(nitrooxyalkyl)benzoate] corticosteroid derivative.

34. The method of claim 33, wherein the base is selected from the group consisting of trimethylamine, pyridine, diisopropyl ethylamine, tetramethylguanidine, 1,5-diazabicyclo[4.3.0]non-5-ene, 1,8-diazabicyclo[5.4.0]undec-7-ene, alkoxides, and carbonates.

35. The method of claim 33, wherein the corticosteroid, the compound of formula (IB), and the base are reacted with a catalyst.

36. The method of claim 35, wherein the catalyst comprises 4-dimethylaminopyridine.

37. The method of claim 33, wherein the 21-hydroxy corticosteroid is selected from the group consisting of alclometasone, aldosterone, beclomethasone, betamethasone, clocortolone, hydrocortisone, budesonide, cortisone, desoximetasone, desonide, dexamethosone, flucloronide, fludrocortisone, flumethasone, flunisolide, fluocinolone acetonide, fluocortolone, fluprednisolone, flurandrenolide, halometasone, methylprednisolone, paramethasone, prednival, prednylidene, prednisolone, prednisone, triamcinolone, and triamcinolone acetonide.

38. The method of claim 33, wherein the 21-hydroxy corticosteroid comprises a 21-hydroxy glucocorticoid.

39. The method of claim 38, wherein the 21-hydroxy corticosteroid comprises prednisolone.

40. The method of claim 33, wherein m is 0, n is 0, $R^5$ is hydrogen, and $R^6$ is hydrogen.

41. The method of claim 33, wherein:

X is Cl or Br; and the corticosteroid, the compound of formula (IB), and the base are reacted with a catalyst.

42. The method of claim 41, wherein the 21-hydroxy corticosteroid comprises a 21-hydroxy glucocorticoid.

43. The method of claim 42, wherein the 21-hydroxy corticosteroid comprises prednisolone.

44. The method of claim 43, wherein m is 0, n is 0, $R^5$ is hydrogen, and $R^6$ is hydrogen.

45. The method of claim 44, wherein the catalyst comprises 4-dimethylaminopyridine and the base comprises trimethylamine.

46. A compound of formula (I):

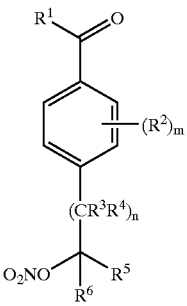

(I)

wherein:

$R^1$ is selected from the group consisting of OH, Cl, Br, F, I, and —OC(O)$R^{10}$;

m is an integer from 0 to 4;

n is an integer from 0 to 5;

$R^2$ is independently selected at each occurrence from the group consisting of amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —O$R^7$;

$R^3$ and $R^4$ are independently selected at each occurrence from the group consisting of hydrogen, amino, substituted amino, halogen, $C_{1-6}$ alkyl, chloroalkyl, alkoxy, aryl, $C_{1-6}$ alkylamino, $C_{1-6}$ substituted alkylamino, and —O$R^7$;

$R^5$ and $R^6$ are independently selected from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —O$R^7$;

$R^7$ is independently selected at each occurrence from the group consisting of hydrogen, —C(O)$R^8$, and —C(O)N$R^1R^9$;

$R^8$ and $R^9$ are independently selected at each occurrence from the group consisting of hydrogen and $C_{1-6}$ alkyl; and $R^{10}$ is selected from the group consisting of $C_{1-6}$ alkyl, $C_{1-6}$ chloroalkyl, alkoxy-substituted $C_{1-6}$ alkyl, and aryl.

47. The compound of claim 46, wherein $R^1$ is OH.

48. The compound of claim 46, wherein $R^1$ is Cl or Br.

49. The compound of claim 47, wherein m is 0, n is 0, $R^5$ is hydrogen, and $R^6$ is hydrogen.

50. The compound of claim 48, wherein m is 0, n is 0, $R^5$ is hydrogen, and $R^6$ is hydrogen.

51. A method for producing a 21-[4'-(nitrooxyalkyl)benzoate] corticosteroid derivative comprising:

(a) reacting a compound of formula (II):

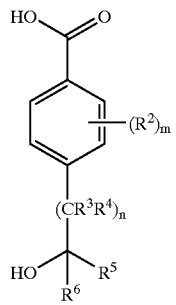

(II)

wherein:
   m is an integer from 0 to 4;
   n is an integer from 0 to 5;
   $R^2$ is independently selected at each occurrence from the group consisting of amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^7$;
   $R^3$ and $R^4$ are independently selected at each occurrence from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and
   $R^5$ and $R^6$ are independently selected from the group consisting of hydrogen, amino, substituted amino, halogen, $C_{1-6}$ alkyl, $C_{1-6}$ haloalkyl, alkoxy, aryl, $C_{1-6}$ alkylamino, $C_{1-6}$ substituted alkylamino, and —$OR^7$;
   $R^7$ is independently selected at each occurrence from the group consisting of hydrogen, —$C(O)R^8$, and —$C(O)NR^8R^9$; and
   $R^8$ and $R^9$ are independently selected at each occurrence from the group consisting of hydrogen and $C_{1-6}$ alkyl;
with acetic anhydride and nitric acid to form a compound of formula (IA):

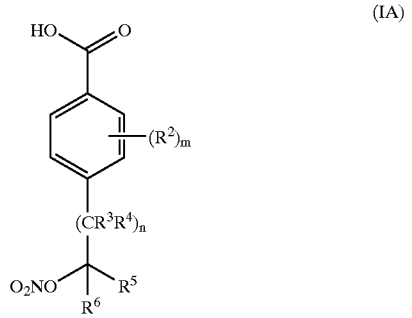

(IA)

wherein m, n, $R^2$, $R^3$, $R^4$, $R^5$, and $R^6$ are as above in the compound of formula (II);
(b) reacting the compound of formula (IA) with an acid anhydride or an acid chloride to form a compound of formula (IC):

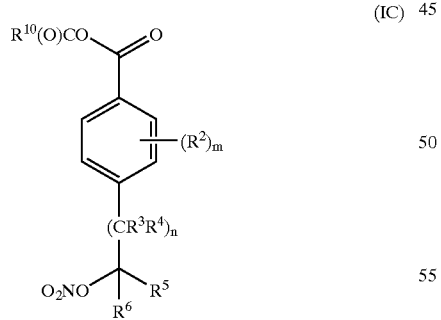

(IC)

wherein:
   m, n, $R^2$, $R^3$, $R^4$ $R^5$, and $R^6$ are as above in the compound of formula (II); and
   $R^{10}$ is selected from the group consisting of $C_{1-6}$ alkyl, $C_{1-6}$ chloroalkyl, alkoxy-substituted $C_{1-6}$ alkyl, and aryl; and
(c) reacting the compound of formula (IC) with a 21-hydroxyalkyl corticosteroid and a base to produce a 21-[4'-(nitrooxyalkyl)benzoate] corticosteroid derivative.

52. The method of claim 51, wherein the base is selected from the group consisting of trimethylamine, pyridine, diisopropyl ethylamine, tetramethylguanidine, 1,5-diazabicyclo[4.3.0]non-5-ene, 1,8-diazabicyclo[5.4.0]undec-7-ene, alkoxides, and carbonates.

53. The method of claim 51, wherein the corticosteroid, the compound of formula (IC), and the base are reacted with a catalyst.

54. The method of claim 53, wherein the catalyst comprises 4-dimethylaminopyridine.

55. The method of claim 51, wherein the 21-hydroxy corticosteroid is selected from the group consisting of alclometasone, aldosterone, beclomethasone, betamethasone, clocortolone, hydrocortisone, budesonide, cortisone, desoximetasone, desonide, dexamethosone, flucloronide, fludrocortisone, flumethasone, flunisolide, fluocinolone acetonide, fluocortolone, fluprednisolone, flurandrenolide, halometasone, methylprednisolone, paramethasone, prednival, prednylidene, prednisolone, prednisone, triamcinolone, and triamcinolone acetonide.

56. The method of claim 51, wherein the 21-hydroxy corticosteroid comprises a 21-hydroxy glucocorticoid.

57. The method of claim 56, wherein the 21-hydroxy corticosteroid comprises prednisolone.

58. The method of claim 51, wherein m is 0, n is 0, $R^5$ is hydrogen, and $R^6$ is hydrogen.

59. The method of claim 51, wherein:
   the base is selected from the group consisting of trimethylamine, pyridine, diisopropyl ethylamine, tetramethylguanidine, 1,5-diazabicyclo[4.3.0]non-5-ene, 1,8-diazabicyclo[5.4.0]undec-7-ene, alkoxides, and carbonates;
   the corticosteroid, the compound of formula (IC), and the base are reacted with a catalyst comprising 4-dimethylaminopyridine;
   m is 0, n is 0, $R^5$ is hydrogen, and $R^6$ is hydrogen; and
   the 21-hydroxy corticosteroid comprises prednisolone.

* * * * *

UNITED STATES PATENT AND TRADEMARK OFFICE
CERTIFICATE OF CORRECTION

PATENT NO. : 6,696,592 B2
DATED : February 24, 2004
INVENTOR(S) : Donald G. McIntyre It is certified that error appears in the above-identified patent and that said Letters Patent is hereby corrected as shown below:

Column 15,
Line 20, delete "$C_1$ alkyl" and insert therefor -- $C_{1-6}$ alkyl --.
Line 32, delete "Cl, Br, F, 1, or" and insert therefor -- Cl, Br, F, I, or --.

Column 16,
Line 55, delete "—$OR^1$;" and insert therefor -- —$OR^7$; --.

Column 18,
Line 42, delete "—$C(O)NO^8R^9$;" and insert therefor -- —$C(O)NR^8R^9$; --.

Column 20,
Line 27, delete "chloroalkyl" and insert therefor -- $C_{1-6}$ haloalkyl --.
Line 37, delete "—$C(O)NR^1R^9$;" and insert therefor -- —$C(O)NR^8R^9$; --.

Column 21,
Line 13, after "alkylamino, and", insert -- —$OR^7$; --.

Signed and Sealed this

Thirteenth Day of July, 2004

JON W. DUDAS
*Acting Director of the United States Patent and Trademark Office*